(12) United States Patent
Kobayashi

(10) Patent No.: US 6,313,204 B1
(45) Date of Patent: Nov. 6, 2001

(54) METHOD FOR RECRYSTALLIZING DIACETAL IN POLYOLEFIN RESIN

(75) Inventor: Toshiaki Kobayashi, Nara (JP)

(73) Assignee: New Japan Chemical Co., Ltd. (JP)

( * ) Notice: Subject to any disclaimer, the term of this patent is extended or adjusted under 35 U.S.C. 154(b) by 0 days.

(21) Appl. No.: 09/341,572
(22) PCT Filed: Jan. 14, 1998
(86) PCT No.: PCT/JP98/00107
§ 371 Date: Jul. 14, 1999
§ 102(e) Date: Jul. 14, 1999
(87) PCT Pub. No.: WO98/31741
PCT Pub. Date: Jul. 23, 1998

(30) Foreign Application Priority Data

Jan. 17, 1997 (JP) .................................. 9-019974

(51) Int. Cl.[7] .................................................. C08K 5/15
(52) U.S. Cl. ............................................................ 524/109
(58) Field of Search ............................................... 524/109

(56) References Cited

U.S. PATENT DOCUMENTS

| | | | |
|---|---|---|---|
| 4,013,619 | * 3/1977 | Schmidt | 260/45.8 |
| 4,963,299 | 10/1990 | Scholtens et al. | |
| 5,120,863 | * 6/1992 | Kobayashi | 549/364 |
| 5,912,292 | * 6/1999 | Sun | 524/301 |

FOREIGN PATENT DOCUMENTS

| | | |
|---|---|---|
| 0 272 015 | 6/1922 | (EP) . |
| 0 569 198 | 11/1993 | (EP) . |
| 0816365 | 1/1998 | (EP) . |
| 3-685579 | 3/1991 | (JP) . |
| 3-169882 | 7/1991 | (JP) . |
| 4-339847 | 11/1992 | (JP) . |
| 7-70134 | 3/1995 | (JP) . |
| 8-157477 | 6/1996 | (JP) . |
| 8-239386 | 9/1996 | (JP) . |

OTHER PUBLICATIONS

Patent Abstracts of Japan, vol. 1997, No. 01, Jan. 31, 1997 & JP 08 239386 A (New Japan Chem Co Ltd), Sep. 17, 1996 *abstract*.

Hideki et al, Japan Patent Abstract No. 07173302, Nov. 11, 1995 Takahiko et al, Japan Patent Abstract No. JP–82–16850.

* cited by examiner

Primary Examiner—Paul R. Michl
(74) Attorney, Agent, or Firm—Larson & Taylor, PLC

(57) ABSTRACT

The present invention relates to a method for recrystallizing diacetal, such as 1,3:2,4-bis-O-(benzylidene)-D-sorbitol or a nuclearly substituted derivative thereof, in a polyolefin resin without giving a yellowish tint to the polyolefin resin; a polyolefin resin molded article containing a recrystallized diacetal which is obtainable by said recrystallization method; a method for producing polyolefin resin pellets containing the recrystallized diacetal by utilizing said recrystallization method, and polyolefin resin pellets obtainable by the above method; and a method for producing a polyolefin resin molded article by heating and melting said pellets at a temperature not lower than its sol-gel transition temperature during the heating cycle and rapidly cooling the melt; and a polyolefin resin molded article obtainable by said method.

16 Claims, No Drawings

METHOD FOR RECRYSTALLIZING DIACETAL IN POLYOLEFIN RESIN

TECHNICAL FIELD

The present invention relates to a method for recrystallizing a diacetal, in particular, a method for recrystallizing a diacetal such as a sorbitol diacetal in a resin composition.

The present invention further relates to a resin molded product containing a diacetal recrystallized by said method.

PRIOR ART

Diacetals such as sorbitol acetal compounds have been known to act as excellent nucleating agents for polyolefin resins, thereby contributing to the improvement in the rigidity, transparency and gloss of the resulting polyolefin resin molded articles, and to the improvement in the efficiency of the molding process.

However, diacetals usually decompose or disproportionate into monoacetal and triacetal when mixed with molten polyolefin resins having a high temperature, resulting in impaired product quality such as yellowish tint given to the molded articles, and also produce odor or staining, thereby posing problems of deteriorating working environment.

Consequently, attempts have been made to solve these drawbacks. For example, a method is a known (Japanese Unexamined Patent Publication No. 120788/1988) which comprises the steps of dissolving a diacetal compound, such as a condensation product of an aromatic aldehyde and a polyhydric alcohol having five or more hydroxyl groups, in a solvent such as dioxane, benzene, xylene, etc; cooling the solution to form a gel; and freeze-drying the obtained gel to give a freeze-dried diacetal having a particular microstructure.

The above method, however, have the shortcomings, for example, of necessitating the use of expensive solvents, large-scale freezer and a special high-vacuum apparatus for freeze-drying, and being not highly productive because only a batchwise production is usually feasible.

DISCLOSURE OF THE INVENTION

The inventors of the present invention carried out extensive research in an attempt to produce diacetal which is free from the above drawbacks. In the course of the research, the inventors of the present invention took a different approach in carrying out further research on the assumption that recrystallization of the above diacetal directly in a polyolefin resin could solve the above drawbacks of the diacetal as a nucleating agent to thereby improve its nucleating effect.

Specifically, the inventors of the present invention considered that the technique of recrystallizing the diacetal directly in a molten polyolefin resin would be an effective technique, if the technique could make it possible to eliminate the necessity of pretreatment such as purification of diacetal, to establish the optimal conditions under which the diacetal best functions as a nucleating agent, and to find manners of preventing diacetal decomposition and resin discoloration, etc.

The research of the inventors, however, revealed that the method of recrystallizing diacetal in a resin is not practically feasible for the following reasons: the diacetal may decompose and emit an odor; the diacetal may undergo disproportionation into monoacetal and triacetal, which lessens the purity of the diacetal; the resin may become tinted yellow, leading to uneven transparency of the molded resins.

In order to prevent the yellowish discoloration of the resins, it may be possible to add a special phosphoric acid-based cooperative stabilizers or to mask the yellowish discoloration by a light scattering of blue colour induced by adding a small amount of a pigment. This method, however, requires expensive cooperative stabilizers or complicated operation, and therefore remains to be improved as an industrial technique.

Therefore, an object of the present invention is to propose a method for recrystallizing diacetal-based nucleating agent composition in a molten polyolefin, wherein decomposition and disproportionation of diacetal and yellowish discoloration of resins are suppressed as much as possible, and wherein the effect of modifying polyolefin resins is produced in an inexpensive manner and to the greatest degree.

The inventors of the present invention carried out extensive research to achieve the above object, and surprisingly discovered that the desired effects can be achieved by recrystallizing, under specific conditions in a molten polyolefin resin, a diacetal nucleating agent composition which satisfies a plurality of specific requirements. The present invention has been accomplished based on this finding.

The present invention provides a method for recrystallizing diacetal represented by the formula (1)

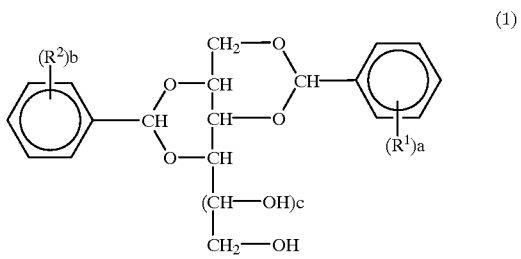

wherein $R^1$ and $R^2$ are the same or different and each represent a hydrogen atom, a $C_1$–$C_4$ alkyl group, a $C_1$–$C_4$ alkoxy group or a halogen atom; a and b each represent an integer of 1 to 5, preferably 1 to 3; c is 0 or 1; when a is 2, the two $R^1$ groups may optionally be taken together with the benzene ring to which they are attached to form a tetralin ring; and when b is 2, the two $R^2$ groups may optionally be taken together with the benzene ring to which they are attached to form a tetralin ring in a polyolefin resin without giving a yellowish tint to the polyolefin resin, the method comprising the steps of:

(i) heating and melting a resin composition comprising (a) a polyolefin resin and (b) a nucleating agent composition comprising at least one diacetal of the above formula (1), at a temperature not lower than the sol-gel transition temperature during the heating cycle of the resin composition, to give a molten resin composition wherein said nucleating agent composition is uniformly dissolved in the molten polyolefin resin; and (ii) cooling the resulting molten resin composition, wherein the above nucleating agent composition satisfies all of the following four requirements (A)–(D) simultaneously:

(A) the above nucleating agent composition contains 10 to 5000 ppm of at least one alkaline compound selected from the group consisting of alkali metal salts, alkali metal hydroxides, alkaline earth metal salts and alkaline earth metal hydroxides, and/or 1000–80000 ppm of an organic amine;

(B) the total amount of
   (B-1) an aromatic aldehyde represented by the formula (2)

(2)

wherein $R^3$ represents a hydrogen atom, a $C_1$–$C_4$ alkyl group, a $C_1$–$C_4$ alkoxy group or a halogen atom; d is an integer of 1 to 5, preferably 1 to 3; when d is 2, the two $R^3$ groups may optionally be taken together with the benzene ring to which they are attached to form a tetralin ring; and (B-2) a dialkyl acetal represented by the formula (3)

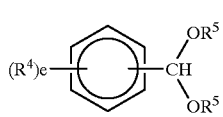

(3)

wherein $R^4$ represents a hydrogen atom, a $C_1$–$C_4$ alkyl group, a $C_1$–$C_4$ alkoxy group or a halogen atom; $R^5$ is a $C_1$–$C_3$ alkyl group; e is an integer of 1 to 5, preferably 1 to 3; when e is 2, the two $R^4$ groups may optionally be taken together with the benzene ring to which they are attached to form a tetralin ring, in the nucleating composition is not higher than 400 ppm;

(C) the water content of said nucleating agent composition is not higher than 1 wt. %; and (D) said resin composition contains said at least one diacetal represented by the formula (1) at a concentration of 0.01–4 wt. % based on the total amount of said polyolefin resin and said diacetal.

In the present invention, it is further preferred that (E) the proportion of position isomers of the diacetal represented by the formula (1) in the above nucleating agent composition is not higher than 0.7 wt. %

In the present invention, it is also preferred that the step of cooling said molten resin composition in the present invention is carried out by rapidly cooling the molten resin composition having a temperature not lower than the sol-gel transition temperature of the resin composition, to 10–80° C., particularly 20–80° C.

The present invention will be described below in detail.

Polyolefin Resin

Useful polyolefin resins in the present invention are crystalline resins having a crystallinity of 50–100%, preferably 15–95%. Specific examples thereof are polyethylene-based resins, stereoregular polypropylene-based resins, and stereoregular polybutene-based resins.

Examples of the polyethylene-based resins are high-density polyethylene, medium-density polyethylene, low-density polyethylene, linear low-density polyethylene, and ethylene copolymers containing 50 wt. % or more of ethylene.

Examples of the polypropylene-based resins are propylene homopolymers and propylene copolymers containing 50 wt. % or more of propylene.

Examples of the polybutene-based resins are homopolymers of butene-1 and butene copolymers containing 50 wt. % or more of butene-1.

Each of the above copolymers may be either random copolymers or block copolymers. Stereoregularity of the above resins may be either isotactic or syndiotactic.

Useful comonomers which may constitute the above copolymers are, for example, α-olefins, particularly a $C_2$–$C_{14}$ α-olefins, such as ethylene, propylene, butene, pentene, hexene, heptene, octene, nonene, decene, undecene, dodecene and the like; bicyclo monomers such as 1,4-endomethylene cyclohexene, (meth)acrylates, particularly $C_1$–$C_8$ alkyl esters of (meth)acrylic acid, such as methyl (meth)acrylate, ethyl (meth)acrylate or the like; vinyl acetate, maleic acid, etc.

Suitable catalysts for producing the above polymers are not only radical catalysts and Ziegler-Natta catalyst which are commonly used, but also supported Ziegler-Natta catalysts comprising a catalyst prepared by depositing a transition metal compound (e.g., titanium halides such as titanium trichloride, titanium tetrachloride, etc.) on a support composed mainly of magnesium halide such as magnesium chloride, in combination with an alkyl aluminum compound (e.g., triethyl aluminum, diethyl aluminum chloride, etc.), or metallocene catalysts.

Recommended melt flow rate (hereinafter abbreviated as "MFR", JIS K 7210-1976) of the polyolefin-based resins for use in the present invention may be suitably selected depending on the molding method to be employed and the physical properties required of the molded article. However, it is usually 0.01–200 g/10 min., preferably 0.05–100 g/10 min. Blends of polyolefin-based resins having different MFR's are also recommended insofar as their MFR's are within the above-specified range.

Nucleating Agent Composition

The nucleating agent composition useful in the present invention comprises, in addition to the diacetal represented by the formula (1), (A) a specific amount of at least one alkaline compound selected from the group consisting of alkali metal salts, alkali metal hydroxides, alkaline earth metal salts and alkaline earth metal hydroxides, and/or a specific amount of an organic amine, and (B) the total amount of the aromatic aldehyde represented by the formula (2) and the dialkyl acetal represented by the formula (3), and (C) the water content are not higher than the respective specific amounts.

The diacetal of the above formula (1) may be known diacetals, or can be prepared by known methods such as disclosed in European Patent No. 497 976, using benzaldehyde having $(R^1)$a group or $(R^2)$b group or its dialkyl acetal and sorbitol or xylitol as the starting materials.

Among the diacetals represented by the above formula (1), there may be mentioned the compound wherein $R^1$ and $R^2$ are the same or different and each represent a hydrogen atom, a $C_1$–$C_4$ alkyl group, a $C_1$–$C_4$ alkoxy group or a halogen atom; a and b each represent an integer of 1 to 5; c is 0 or 1.

Among these compounds, preferable are the compounds represented by the formula (1) wherein $R^1$ and $R^2$ each represent a $C_1$–$C_4$ alkyl group or a halogen atom, in particular a chlorine atom; a and b each represent 1 or 2 or 3; and c is 1.

Although various kinds of diacetals may be used according to the present invention, preferable are those which have been conventionally used as nucleating agents for polyolefin resins. In particular, effective is/are at least one compound selected from the group consisting of
1,3:2,4-bis-O-(benzylidene)-D-sorbitol,
1,3:2,4-bis-O-(p-methylbenzylidene)-D-sorbitol,
1,3:2,4-bis-O-(p-ethylbenzylidene)-D-sorbitol,
1,3:2,4-bis-O-(2,4-dimethylbenzylidene)-D-sorbitol,
1,3:2,4-bis-O-(3,4-dimethylbenzylidene)-D-sorbitol,
1,3:2,4-bis-O-(3,5-dimethylbenzylidene)-D-sorbitol, 1,3:2,4-bis-O-(2,4,5-trimethylbenzylidene)-D-sorbitol,
1,3:2,4-bis-O-(p-chlorobenzylidene)-D-sorbitol,
1,3:2,4-bis-O-(tetrahydronaphthylidene-D-sorbitol,
1,3-O-benzylidene-2,4-O-(2,4-dimethylbenzylidene)-D-sorbitol,
1,3-O-(2,4-dimethylbenzylidene)-2, 4-O-benzylidene-D-sorbitol,
1,3-O-benzylidene-2,4-O-(3,4-dimethylbenzylidene)-D-sorbitol, and
1,3-O-(3,4-dimethylbenzylidene)-2,4-O-benzylidene-D-sorbitol.

Among those compounds, effective is/are at least one compound selected from the group consisting of:
1,3:2,4-bis-O-(benzylidene)-D-sorbitol,
1,3:2:4-bis-O-(p-methylbenzylidene)-D-sorbitol,
1,3:2:4-bis-O-(p-ethylbenzylidene)-D-sorbitol,
1,3:2,4-bis-O-(2,4-dimethylbenzylidene)-D-sorbitol,
1,3:2,4-bis-O-(3,4-dimethylbenzylidene)-D-sorbitol,
1,3:2,4-bis-O-(2,4,5-trimethylbenzylidene)-D-sorbitol, and
1,3:2,4-bis-O-(p-chlorobenzylidene)-D-sorbitol.

(A) The nucleating agent composition of the present invention contains, based on the nucleating agent composition, (i) 10–5000 ppm, preferably 50–2000 ppm, of at least one alkaline compound selected from the group consisting of alkali metal salts, alkali metal hydroxides, alkaline earth metal salts and alkaline earth metal hydroxides, and/or (ii) 1000–80000 ppm, preferably 10000–60000 ppm (1–6 wt. %), of an organic amine. Presumably, these compounds act as decomposition inhibitors and disproportionation inhibitors for the diacetals.

Addition of said at least one alkaline compound selected from the group consisting of alkali metal salts, alkali metal hydroxides, alkaline earth metal salts and alkaline earth metal hydroxides, and/or said organic amine, in an amount greater than the above specified respective amounts, to the diacetal before recrystallization would not remarkably improve the effect of suppressing diacetal decomposition and disproportionation of the diacetal during the step of recrystallization by dissolving and cooling the diacetal, leading to discoloration of matrix resins.

On the other hand, when the amounts of the additives are less than the above specified respective amounts, the effect of suppressing diacetal decomposition and disproportionation during the recrystallization step would not be produced, and the resin would markedly tend to have a yellowish tint.

Examples of the above alkaline compounds are hydroxides of alkali metals, such as potassium hydroxide, sodium hydroxide and lithium hydroxide; alkali metal carbonates such as sodium carbonate and potassium carbonate; alkali metal salts of benzoic acid, such as sodium benzoate and potassium benzoate; alkali metal salts, such as sodium salts, potassium salts or lithium salts of nuclear-substituted aromatic carboxylic acids such as benzoic acid having, for example, 1 to 4, preferably 1 to 3, substituents selected from a $C_1$–$C_5$ alkyl group, a $C_1$–$C_5$ alkoxy group or a halogen atom (e.g., chlorine atom, bromine atom, fluorine atom, etc.); sodium salt, potassium salt and lithium salt of glutamic acid; alkali metal salts, such as sodium salts and potassium salts, of $C_1$–$C_{24}$ fatty acids or $C_2$–$C_{24}$ hydroxy fatty acids, especially monohydroxy fatty acids.

Among these, more preferable are sodium salts and potassium salts of $C_{12}$–$C_{24}$ fatty acids. Examples thereof are sodium laurate, sodium stearate, sodium behenate, sodium 12-hydroxyoctadecanoate, etc.

Among such alkali metal hydroxides and alkali metal salts, preferred are potassium hydroxide, sodium hydroxide, lithium hydroxide, potassium carbonate, sodium benzoate; sodium salts or potassium salts of benzoic acid having one or more alkyl groups, alkoxy groups or halogen atoms as the substituent(s), potassium salts, sodium salts or lithium salts of glutamic acid; or sodium salts or potassium salts of $C_1$–$C_{24}$ fatty acids or $C_2$–$C_{24}$ hydroxy fatty acids. Sodium carbonate, potassium benzoate and the like are preferred as well.

Among these, recommended are sodium hydroxide, potassium hydroxide, potassium salts of aromatic carboxylic acids having, for example, one or two alkyl groups ($C_1$–$C_4$) substituting on a benzene ring, such as potassium p-methylbenzoate, potassium 2,4-dimethylbenzoate, etc.

Examples of the alkaline earth metal hydroxides include hydroxides of magnesium and calcium. Preferred alkaline earth metal salts are carbonates of magnesium and calcium; magnesium salts and calcium salts of known organic carboxylic acids, especially calcium salts and magnesium salts of $C_{12}$–$C_{24}$ fatty acids.

Recommendable organic amines are N,N-diethanol-($C_{12}$–$C_{24}$)alkylamine, N,N-di($C_{12}$–$C_{24}$)alkylmethylamine, trisisopropanolamine, etc. Especially N,N-diethanolstearylamine, N,N-diethanolbehenylamine, and N,N-distearylmethylamine are more recommendable.

(B) The total amount of the aldehydes selected from the group consisting of the aromatic aldehyde represented by the above formula (2) and the dialkyl acetal represented by the above formula (3) contained in the nucleating agent composition is not higher than 400 ppm, preferably not higher than 200 ppm, more preferably not higher than 100 ppm.

That is, the aromatic aldehyde represented by the formula (2) and the dialkyl acetal represented by the general formula (3) need not be present in the nucleating agent composition. When only one of the aromatic aldehyde or the dialkyl acetal is contained in the nucleating agent composition, the amount thereof is 400 ppm or less. When both of the aldehyde and the dialkyl acetal are contained, the total amount is 400 ppm or less.

If the above amount exceeds 400 ppm, the resin composition or the resulting molded resin articles containing recrystallized diacetal become tinted yellow to a greater degree, and the amount of decomposed aldehyde is undesirably increased.

In order to limit the total amount of the aldehydes selected from the group consisting of aromatic aldehyde represented by the formula (2) and the dialkyl acetal represented by the formula (3) to 400 ppm, various methods can be employed. Such method may comprise purification by extraction, for example, by washing the diacetal, immediately after preparation, with water or a suitable organic solvent such as n-hexane, toluene, xylene, methanol, ethanol, isopropanol, cyclohexane, etc.; or may comprise drying the diacetal, immediately after preparation, under reduced pressure to remove the above aromatic aldehyde and dialkyl acetal from the system until the concentration thereof becomes not higher than the above-mentioned concentration.

(C) The water content of the nucleating agent composition is not higher than 1 wt. %, preferably not higher than 0.3 wt. %. If the water content is higher than 1 wt. %, resin compositions containing recrystallized diacetal becomes tinted yellow to a greater degree, and the amount of decomposed aldehyde is undesirably increased.

Various methods can be employed to limit the water content of the nucleating agent composition to 1 wt. % or less. Typical method comprises drying the nucleating agent composition to be subjected to recrystallization, under reduced pressure and at a temperature maintained to 40° C.

to 100° C., or carrying out the purification using a hydrophilic organic solvent such as a lower alcohol. Although being complicated, another method may also be used which comprises suspending the nucleating agent composition to be subjected to recrystallization, in a solvent such as methanol, isopropanol or the like to form a slurry, and then filtering the slurry, followed by drying.

At this stage, (i) at least one alkaline compound selected from the group consisting of alkali metal salts, alkali metal hydroxides, alkaline earth metal salts and alkaline earth metal hydroxides, and/or (ii) an organic amine, mentioned in section (A) above, can be dissolved in advance in the above solvent so that the specific amount(s) of the component(s) (i) and/or (ii) can be contained in the nucleating agent composition.

The method for preparing the nucleating agent composition for use in the present invention is not particularly limited, and may comprise, for example, uniformly mixing a diacetal represented by the above formula (1), wherein the total amount of the aromatic aldehyde represented by the formula (2) and the dialkyl acetal represented by the formula (3) is 400 ppm or less, preferably 200 ppm or less, with the specific amount of at least one alkaline compound selected from the group consisting of alkali metal salts, alkali metal hydroxides, alkaline earth metal salts and alkaline earth metal hydroxides, and/or an organic amine, and adjusting the water content of the resulting mixture to 1 wt. % or less.

Furthermore, according to a preferred embodiment of the present invention, (E) it is preferable that the content of the position isomers of the diacetal represented by the formula (1) in the nucleating agent composition of the present invention is 0.7 wt. % or less, more preferably 0.4 wt. % or less.

Herein, the position isomers of diacetal represented by formula (1) refers to structural isomers wherein two benzylidene groups are bonded to other positions than 1,3:2,4-, such as 1,2:3,4-bis-O-(benzylidene)-D-sorbitol, 1,2:3,4-bis-O-(3,4-dimethylbenzylidene)-D-sorbitol and 1,2:3,4-bis-O-(p-methylbenzylidene)-D-sorbitol.

The amount of such position isomers of the diacetal is the amount measured by extracting the nucleating agent composition completely, for example, using cyclohexane, for example, by Soxhlet extraction for 4 to 12 hours, filtering the composition at atmosphere, drying the filtrate, and analyzing the residue by gas chromatography.

If the amount of the position isomers is greater than 0.7 wt. %, especially greater than 0.8 wt. %, the resin compositions tend to become tinted yellow to some greater degree, and the amount of decomposed aldehyde tends to increase.

The proportion of the position isomers of the diacetal can be limited to 0.7 wt. % or below, for example, by one of the following methods: dispersing the nucleating agent composition of the present invention in hot water, followed by filtration; or washing the nucleating agent composition with an organic solvent such as methanol, hexane or the like; or selectively hydrolyzing the position isomers with use of an acid catalysts, such as paratoluenesulfonic acid, sulfuric acid or phosphoric acid, in a slurry which is obtained during the production of a diacetal and which contains the formed diacetal as dispersed in an organic solvent such as toluene, xylene or cyclohexane or water serving as the reaction solvents, the position isomers being dissolved in the organic solvent serving as the reaction solvents or dispersed in water acting as the dispersion solvent.

Recrystallization

After preparing the nucleating agent composition so that the above requirements (A), (B) and (C) can be satisfied, the nucleating agent composition of the present invention is blended with a polyolefin resin to give a resin composition. By subjecting the thus-obtained resin composition to (1) a step of producing a molten resin composition and (2) a step of cooling the molten resin composition, under respective specific conditions, diacetal crystals are formed in the polyolefin resin in the form of fibrils having a diameter in the order of nanometers without imparting a yellowish tint to the polyolefin resin.

Specifically, upon cooling the molten resin composition according to the process of the present invention, the diacetal is recrystallized, affording crystals in the form of protofibrils, or a mixture of protofibrils and bundled crystals consisting of a plurality of assembled protofibrils.

In this specification and claims, crystals in the form of protofibrils and crystals in the form of bundles are collectively referred to as "fibrils".

These fibrils typically range from about 9 to 1000 nm, in particular 9 to 400 nm, in cross-sectional diameter perpendicular to the longitudinal direction of the fibril. The fibrils form a coarse network in polyolefin resin matrix.

In this specification and claims, the terms "protofibrils", "bundles" or "bundled crystals" used are intended to mean the following:

Among the diacetal crystals in the form of fibrils as described above, the smallest crystals present in a non-assembled form, especially singular fibrils which are typically about 9 to 20 nm in cross-sectional diameter perpendicular to the longitudinal direction of the fibril, are called "protofibrils".

In addition, among the diacetal crystals in the form of fibrils as described above, the crystals which are composed of a plurality of the above protofibrils assembled in bundles and which are typically about 20 to 1000 nm, particularly 20 to 400 nm, in diameter in cross-section perpendicular to the longitudinal direction of the fibers of the bundle, are called "bundles" or "bundled crystals".

Further, in this specification and claims, the diameter of the cross-section perpendicular to the longitudinal direction of the protofibrils, of bundles or bundled crystals, or of fibrils is simply referred to as "diameter" for convenience.

(1) A Step of the Preparation of a Molten Resin Composition

In the recrystallization method of the present invention, first, the nucleating agent composition of the present invention, satisfying the above requirements (A), (B) and (C), is uniformly dissolved in a melt of the polyolefin to provide a molten resin composition.

In the present invention, (D) the amount of the diacetal represented by the formula (1) is adjusted to 0.01 to 4 wt. %, preferably 0.05 to 2.0 wt. %, based on the total amount of the polyolefin resin and the diacetal represented by the formula (1). The diacetal is then recrystallized in the molten polyolefin under certain conditions.

This procedure makes it possible to provide the recrystallized diacetal crystals comprising the protofibrils about 9 to 20 nm in diameter in a higher proportion relative to the amount of all the fibrils (i.e., protofibrils and bundled crystals), in the polyolefin resin.

The higher the proportions of protofibrils having smaller diameter is, the larger the surface area of the diacetal crystals per unit weight is, and this would be why the nucleating effects are improved.

When the concentration of the diacetal represented by the above formula (1) is lower than 0.01 wt. %, the desired nucleating effects are not produced. On the other hand, if the concentration is higher than 4 wt. %, the fibrils formed by recrystallization in the resin become very large in diameter, regardless of the recrystallization conditions, consequently scattering light to impair the transparency of the resin, and significantly decreasing the nucleating properties.

Optionally, the nucleating agent composition of the present invention may be used in combination with other additives for polyolefin, which have been conventionally known in the art, within the scope of the objects of the present invention.

As such additives for polyolefins, there can be mentioned various additives listed in "The Tables of Positive Lists of Additives", edited by Japan Hygienic Olefin and Styrene Plastic Association (January 1995), for instance. Specific examples are stabilizers (metal compounds, epoxy compounds, nitrogen compounds, phosphorus compounds, sulfur compounds, etc.), UV absorbers (benzophenone-based compounds, benzotriazole-based compounds, etc.), antioxidants (phenol-based compounds, phosphite-based compounds, sulfur-based compounds, etc.), surfactants (higher fatty acid monoglycerides, polyoxyethylene alkyl ethers, etc.), lubricants or neutralizers (aliphatic hydrocarbons such as paraffins and waxes, $C_8$–$C_{22}$ higher fatty acids, $C_8$–$C_{22}$ higher fatty acid metal (Al, Zn) salts, $C_{12}$–$C_{22}$ higher alcohols, polyglycols, esters of a $C_4$–$C_{22}$ higher fatty acid and a $C_4$–$C_{18}$ aliphatic monohydric alcohol, $C_8$–$C_{22}$ higher fatty acid amides, silicone oils, rosin derivatives, etc.), fillers (talc, hydrotalcite, mica, zeolite, perlite, diatomaceous earth, glass fiber, etc.), blowing agents, auxiliary blowing agents, and polymer additives, and additionally include various additives such as crosslinking agents, crosslinking accelerators, fire retardants, dispersants, processing aids, etc.

Among the above additives, it is preferable that a $C_{12}$–$C_{22}$ higher fatty acid monoglyceride or a $C_{12}$–$C_{22}$ higher fatty acid amide is used in a proportion of 5 to 100 wt. %, particularly 10 to 50 wt. %, based on the nucleating agent composition, since the use thereof improves the transparency of the resin.

The molten resin composition of the present invention may be prepared, for example, by uniformly dry-blending the nucleating agent composition of the present invention, a polyolefin resin and if desired the above known additives for polyolefin resins with a conventional mixer such as Henschel mixer at room temperature to give a resin composition; heating and melting the resulting resin composition at a temperature not lower than the sol-gel transition temperature of said resin composition, which is variable depending on the amount of diacetal and other factors, for example, at a temperature of about 140 to 270° C., preferably 180 to 260° C.; and uniformly dissolving the nucleating agent composition in the molten polyolefin resin.

Herein, sol-gel transition temperature during the heating cycle means the temperature determined by the following procedure. First, a polyolefin resin, a nucleating agent composition and if desired the above additives are dry-blended. The resulting resin composition is heated to give a uniform molten resin composition, which is then maintained at 140° C. to 150° C. for 20 minutes to form a gel. The gel at 140° C. to 150° C. is heated again. Then, the temperature at which the gel becomes a uniform molten resin composition (sol) is measured. This temperature is referred to as a sol-gel transition temperature during the heating cycle.

The sol-gel transition temperature of the above resin composition may be readily determined using a rheometer [see, for example, Toshiaki Kobayashi et al., Journal of the Society of Rheology, Japan, 18, (1), 44 (1990)].

The sol-gel transition temperature may vary depending on the type of resin and the type and composition of the additives to be added if so desired. For example, the sol-gel transition temperature during the heating cycle of the resin composition which, for example, contains 0.1 to 0.5 wt. % of the diacetal and at least 90 wt. % of a resin, based on the resin composition, is usually about 190 to 230° C. when the resin is a polypropylene resin, about 170 to 220° C. when the resin is a polyethylene resin, and about 190 to 220° C. when the resin is a polybutene-1 resin.

(2) Recrystallizing Step

The recrystallization method according to the present invention comprises a step of cooling the above molten resin composition.

The temperature of the molten resin composition and the temperature at which the molten resin composition is cooled can be selected from a relatively wide range. However, from the standpoint of providing diacetal crystals in the form of fibrils having a diameter in the order of nanometers (about 9 to 1,000 nm) by controlling the recrystallization step, without giving a yellowish tint to the polyolefin resin and with a view to achieving an optimal nucleating properties, it is preferable that the molten resin composition is prepared at a temperature not lower than the sol-gel transition temperature during the heating cycle of said resin composition, and the molten resin composition is rapidly cooled to about 10° C. to 80° C., particularly 20 to 80° C., preferably 25 to 50° C.

According to a preferred embodiment of the present invention, a resin composition containing the nucleating agent composition of the present invention, a polyolefin resin and if desired the above known additives for polyolefin resins is heated at a temperature not lower than the sol-gel transition temperature during the heating cycle of said resin composition, until the resin composition becomes a uniform solution (sol state) to give a molten resin composition, and thereafter the step of recrystallizing the diacetal is carried out by injection- or press-molding said molten resin composition under a rapid cooling condition in which the mold temperature is set to about 10 to 80° C., in particular to about 20 to 80° C., preferably to about 25 to 50° C., or the step of recrystallizing the diacetal is carried out by extrusion-molding said molten resin composition under a rapid cooling condition in which the chill roll temperature or water-cooling temperature is set to the same temperature (about 10 to 80° C., in particular about 20 to 80° C., preferably about 25 to 50° C.). Then, the diacetal crystals consisting of protofibrils ranging in diameter from 9 to 20 nm or diacetal crystals wherein the proportion of such protofibrils is 50 vol. % or more relative to all the fibrils can be provided in the resulting resin molded products.

The research carried out by the inventors of the present invention has revealed that (i) when the recrystallized diacetal present in the molded resin articles consists essentially of the above protofibrils 9 to 20 nm in diameter, and (ii) when the recrystallized diacetal present in the molded resin articles is in the form of mixed crystals comprising at least 50 vol. % of the protofibrils 9 to 20 nm in diameter and additionally comprising bundled crystals composed of the protofibrils assembled (and optionally comprising the protofibrils having diameters outside of the above-specified range), especially excellent nucleating effects such as improved physical properties including transparency, gloss and tensile strength of the resulting resin molded articles, increased crystallization rate of the polyolefin resins or the like are produced to a maximum degree.

In order to produce such excellent nucleating effects, it is the first priority to control a temperature of the molten resin composition to a temperature which is not lower than the sol-gel transition temperature during the heating cycle of said resin composition, as described above. If the temperature of the molten resin composition is lower than the sol-gel transition temperature during the heating cycle, the transparency, for example, of the obtained molded articles is decreased so that the nucleating effects are not fully produced.

In order to produce the above excellent nucleating effects, it is also important that the specific cooling conditions must be employed during the recrystallization step. That is, concerning the above temperature conditions in the recrystallization step of the present invention, if the cooling temperature in the cooling step, such as a mold temperature in injection molding or press molding or a chill roll temperature or a water cooling temperature in extrusion molding, is set to a temperature higher than 90° C., then the tendency that the diameters of the resulting fibrils exceed 20 nm increases, presumably because the recrystallization in a non-equilibrium state takes place under a small temperature gradient, with the result that the nucleating effect is reduced and the transparency of the resin is not very successfully improved. In addition, if a mold temperature, or chill roll temperature, or cooling water temperature is set to a temperature lower than 10° C., the nucleating effect is lowered and the transparency of the resin is difficult to improve, presumably because the molecular diffusion rate of the molten resin is suppressed.

In view of the above, the present invention provides a method for recrystallizing diacetal or a method for producing a molded resin composition, the method comprising heating the resin composition of the present invention at a temperature not lower than its sol-gel transition temperature during the heating cycle in an injection molder, press molder or an extrusion molder to give a molten resin composition, and injection-molding, press-molding or extrusion-molding the molten resin composition under a large temperature gradient by rapidly cooling the molten resin composition to a temperature of 10 to 80° C.

Production of Polyolefin Resin Composition Pellets

According to the present invention, a strand can be obtained by the above extrusion molding method, and therefore, by cooling and cutting the strand, a resin composition pellets (hereinafter referred to as "pellets") comprising recrystallized diacetal crystals in the form of fibrils can be obtained.

Therefore, the present invention provides a process for producing pellets comprising the steps of heating a resin composition containing the nucleating agent composition of the present invention to a temperature which is not lower than its sol-gel transition temperature during the heating cycle to give a molten resin composition; and carrying out an extrusion-molding, via the recrystallization step according to the present invention in which the molten resin composition is rapidly cooled, preferably rapidly cooled to 10–80° C., in particular to 20–80° C.

More specifically, the present invention provides a process for producing polyolefin resin pellets which comprises a diacetal represented by the above formula (1) in the form of fibrils recrystallized in the polyolefin resin, and which is substantially free from a yellowish tint, the process comprising the steps of:

(i) heating and melting a resin composition containing (a) a polyolefin resin and (b) a nucleating agent composition containing at least one diacetal represented by the above formula (1) at a temperature not lower than the sol-gel transition temperature during the heating cycle of said resin composition to thereby prepare a molten resin composition, wherein the above nucleating agent composition is uniformly dissolved in the molten polyolefin resin;

(ii) extruding the thus-obtained molten resin composition and cooling the extrudate (generally to 10–80° C., particularly to 20–80° C., preferably to 25–50° C.); and (iii) cutting the thus-obtained polyolefin resin strand containing the recrystallized diacetal, wherein (A) the above nucleating agent composition contains 10–5000 ppm of at least one alkaline compound selected from the group consisting of alkali metal salts, alkali metal hydroxides, alkaline earth metal salts and alkaline earth metal hydroxides, and/or 1000–80000 ppm of an organic amine;

(B) the total amount of
(B-1) an aromatic aldehyde represented by the formula (2)

(2)

wherein $R^3$ represents a hydrogen atom, a $C_1$–$C_4$ alkyl group, a $C_1$–$C_4$ alkoxy group or a halogen atom; d is an integer of 1 to 5, preferably 1 to 3; and when d is 2, the two $R^3$ groups may optionally be taken together with the benzene ring to which they are attached to form a tetralin ring, and (B-2) a dialkyl acetal represented by the formula (3)

(3)

wherein $R^4$ represents a hydrogen atom, a $C_1$–$C_4$ alkyl group, a $C_1$–$C_4$ alkoxy group or a halogen atom; R5 represents a $C_1$–$C_3$ alkyl group; e is an integer of 1 to 5, preferably 1 to 3; and when e is 2, the two $R^4$ groups may optionally be taken together with the benzene ring to which they are attached to form a tetralin ring, in said nucleating agent composition is not higher than 400 ppm, preferably not higher than 200 ppm;

(C) the water content of the nucleating agent composition is not higher than 1 wt. %; and (D) said resin composition contains 0.01–4 wt. % of the diacetal represented by the formula (1), based on the total amount of the polyolefin resin and the diacetal.

According to this process, production efficiency (speed) of the pellets is remarkably increased, due to the nucleating effects of the recrystallized diacetals. In addition, the use of the above pellets in a molding process greatly shortens the processing cycle time, and gives substantially no yellowish tints to the molded articles.

Processing Using the Polyolefin Resin Composition Pellets of the Present Invention Furthermore, the research of the present inventors has revealed that, regardless of the type of the molding method employed, by rapidly cooling, under the above specified conditions, the molten resin composition containing the nucleating agent composition of the present invention as uniformly dissolved therein at the above specified concentration, the diacetal contained in said molten resin composition is recrystallized, and the obtained molded articles contain the desired diacetal crystals, in particular the diacetal crystals which comprises 50 vol. % or more, based on all fibrils, of protofibrils 9 to 20 nm in diameter, and which further comprises bundled crystals consisting of the protofibrils assembled in the form of bundles (and which may further comprise protofibrils larger than 20 nm in diameter). Moreover, the resulting molded articles were found to be substantially free from a yellowish tint.

Consequently, molded articles containing recrystallized diacetal and substantially free from a yellowish tint can be provided by injection-, press- or extrusion-molding the molten resin composition having a temperature not lower than the sol-gel transition temperature during the heating cycle of the resin composition and containing the nucleating agent composition of the present invention using an injection molder, a press molder or an extrusion molder, in which the molten resin composition is rapidly cooled generally to 10–80° C., in particular to 20–80° C., preferably to 25–50° C. In the thus-obtained molded articles, recrystallized diacetal crystals, which can optimally act as a clarifying nucleating agent, are present in the form of fibrils, especially in the form of a network constituted by the fibrils.

In a molding method comprising the first step of pelletizing the resin composition and the second step of subjecting the pellets to a molding operation as well, the use of the above recrystallization conditions in each step provides recrystallized diacetal, which optimally functions as a clarifying nucleating agent, without giving a yellowish tint to the resins.

Specifically, as described with respect to the above-mentioned method for producing pellets according to the present invention, the resin composition pellets of the present invention substantially free from a yellowish tint can be prepared by heating a resin composition containing a polyolefin resin, the specific amount of the nucleating agent composition of the present invention and one or more optional additives at a temperature not lower than the sol-gel transition temperature during the heating cycle of said resin composition to give a molten resin composition, subsequently extrusion-molding the molten resin composition and cutting the strand containing the recrystallized diacetal.

By heating and melting the above resin composition pellets at a temperature not lower than the sol-gel transition temperature during the heating cycle thereof and subsequently injection-, press- or extrusion-molding the melt under rapid cooling to a temperature of 10–80° C., in particular 20–80° C., preferably 25–50° C., diacetal crystals in the form of fibrils are first formed in the cooling step and act as a nucleating agent, whereby the polyolefin crystallizes to give a resin molded articles having good transparency and rigidity. In the obtained molded articles, recrystallized diacetal, which can optimally act as a clarifying nucleating agent, is again present in the form of fibrils, in particular in the form of a network.

Resin Molded Articles Containing Recrystallized Diacetal

The resin molded articles, in particular injection-, press- and extrusion-molded articles, containing the diacetal recrystallized in a polyolefin resin by the above recrystallization method of the present invention, are excellent in rigidity, transparency, gloss, etc. Especially, their transparency is high, and the degree of their discoloration is extremely low, and the degree of formation of the starting acetal caused by the decomposition or disproportionation of diacetal during the molding process is also quite low.

The pellets produced by the process for preparing the pellets according to the present invention are subjected to a molding process such as injection molding, sheet molding, blow molding, press molding or the like, while satisfying the above diacetal recrystallization conditions of the present invention. This molding process is carried out preferably by heating the pellets at a temperature not lower than the sol-gel transition temperature during the heating cycle thereof to give a uniform molten resin composition, and molding the molten resin composition with cooling to a temperature of 10–80° C., in particular 20–80° C., preferably 25–50° C.

Again, in the thus-obtained molded articles which are substantially free from a yellowish tint, the recrystallized diacetal is in the form of diacetal crystals wherein the proportion of the protofibrils 9 to 20 nm in diameter is 50 vol. % or more based on all fibrils, and exhibits favorable nucleating effects.

Therefore, the thus-obtained molded polyolefin resin composition are excellent in rigidity, transparency, gloss, etc. Particularly, their transparency is superior, and the molded articles have extremely low degree of discoloration, and the degree of aromatic aldehyde generation caused by the decomposition or disproportionation of diacetal during molding processing is also very low.

When the cooling temperature during molding processing is 90° C.–140° C., the proportion of the crystals having diameters of 40 nm or larger, namely bundled crystals composed of assembled protofibrils of recrystallized diacetal, tends to increase. This can be one of the reasons for producing the tendency toward the impaired nucleating effects of the diacetal.

Both the polyolefin resin molded articles directly obtainable by a recrystallization method of the present invention, and the polyolefin resin molded articles which is obtainable by the molding process using the resin composition pellets of the present invention and which contains re-recrystallized diacetal crystals containing at least 50 vol. % of diacetal protofibrils 9 to 20 nm in diameter based on all fibrils, are useful as containers, sheets, films, etc., and are substantially free from a yellowish tint, and have excellent transparency.

Therefore, the molded articles of the present invention are highly useful for applications in which transparency is required, such as containers and packaging of foodstuffs and cosmetics, cases for clothing, stationery, machine tools, medical equipment, cases for electrical appliances, furniture, sheds, containers, etc.

EXAMPLES

Examples are given below to illustrate the present invention in further detail.

Preparation of the resin composition pellets and sheets and measurement of the properties in the Examples and Comparative Examples were carried out as follows.

(1) Method for Preparing Pellets and Method for Preparing Sheets

A 100 wt. part quantity of random polypropylene (propylene-ethylene copolymer containing 2 wt. % of ethylene, MFR=6 g/10 min.), 0.03 wt. part of calcium stearate, 0.03 wt. part of Irganox 1010 (trade name, product of Ciba-Geigy), 0.06 wt. part of Irgafos 168 (trade name, product of Ciba-Geigy), and the nucleating agent composition of each of the examples were dry-blended. The resulting dry-blend was mixed within an extruder at 240° C. to give a uniform solution. The uniform solution was extruded to produce a molten resin strand, which was then rapidly cooled by immersing in water at 30° C. so as to effect the contemplated recrystallization of the diacetal. Then, the strand was cut into pellets.

These pellets were made into two types of sheets, one being 4.0 mm in thickness and the other being 1.0 mm in thickness, by an injection molding method wherein the pellets were melted in an injection-molder which was set to give a molten resin temperature of 250° C., and wherein the melt was rapidly cooled by setting a mold temperature to 40° C. with a retention time of 20 seconds (40° C.×20 sec.).

(2) Amount of Alkaline Compound

The amounts of the alkaline compound containing alkali metal or alkaline earth metal in the molecule or the amine added during the preparation of the nucleating agent composition are shown in Table 1. The amount of the metal in the alkaline compound was determined by atomic-absorption spectroscopy.

(3) Water Content

A nucleating agent composition (1.0 g) was dissolved in 50 ml of NMP (N-methylpyrrolidone) at room temperature, and quantitative analysis was conducted by the Karl Fischer method.

(4) The Amount of an Aromatic Aldehyde of the Formula (2) and a Dialkyl Acetal of the Formula (3), and the Amount of Diacetal Position Isomers, in the Nucleating Agent Composition A nucleating agent composition (1.0 g) was extracted with 50 ml of cyclohexane for 12 hours by means of a Soxhlet extractor. The resulting mother liquor was filtrated at atmosphere, and the cyclohexane was removed by topping at room temperature. The resulting residue was quantitatively analyzed by the internal standard method of GC analysis. n-Octanol was used as the internal standard. The amount of the dialkyl acetal represented by the formula (3) in the nucleating agent composition used in each of Examples and Comparative Examples below was 0 ppm.

(5) Degree of Discoloration of the Pellets and Sheets

Visually evaluated for the degree of a yellowish tint, in comparison with the sheet made of a resin alone (Comparative Example 1). The 4.0-mm thick sheets were used.

o: No difference from the sheet made of the resin only is observed

X: A yellowish tint is observed.

(6) Transparency

Measured according to JIS K 7105 using a haze meter with respect to 1.0-mm thick sheet sheets.

(7) Degree of Diacetal Decomposition

Ten 1.0 mm-thick sheets (30×70 mm) were immersed in 300 ml of water at 75° C., and maintained in a thermostat at 75° C. for 3 hours. The amount of the extracted aromatic aldehyde represented by the formula (2) was determined by gas chromatography, and the amount of aldehyde generated during the molding processing was calculated.

The calculation was carried out in the following manner: all the aldehyde within the sheet was extracted with hot water. The amount of an aldehyde initially contained in the nucleating agent composition was subtracted from the amount of the extracted aldehyde. The resulting value was the amount of aldehyde generated during the production of pellets or sheets, and was expressed in terms of the concentration (ppm) in the sheet.

(8) The Diameters of the Protofibrils Constituting the Fibrils of Diacetal Crystals in a Gel, and the Proportion of the Protofibrils Relative to all Fibrils The nucleating agent composition each of the examples was mixed and dissolved in atactic polypropylene (MFR=45 g/10 min.) at 240° C., in an amount used in each of the examples. The solution was rapidly cooled in water at 30° C. to give a diacetal gel.

Ten replicas, per sample gel, of fracture surface were prepared. These replicas were observed using a scanning electron microscope (SEM), and the diameters and the proportion (vol. %) of the protofibrils of recrystallized dialectal in the gel was determined. At the same time, an ultra thin section of the gel was exposed to a $RuO_4$ gas to stain the fibrils therein. Then the section was observed using a transmission electron microscope (TEM) to determine the diameters and the proportion (Vol. %) of the protofibrils of the recrystallized diacetal.

Diacetal, dispersed at the molecular level (dissolved) in the molten polypropylene at a temperature not lower than the sol-gel transition temperature, recrystallizes in the form of fibrils in the molten polypropylene as its temperature falls. Crystallization of polypropylene is considered to start from the active sites on the surface of the fibrils.

The recrystallization process of the diacetal represented by the formula (1) takes place in an amorphous molten polypropylene resin serving as a matrix. Therefore, the diameters of the fibrils of the diacetal crystals formed by recrystallization are independent of the stereoregularity of the polypropylene resin itself. For this reason, regardless of whether the polypropylene, namely the resin serving as the matrix in the molten state, is amorphous or stereoregular, the diameters of the fibrils to be formed in both cases are supposed to be of equal size.

Consequently, amorphous atactic polypropylene can be used as a model matrix for forming fibrils.

Example 1

Using 0.25 wt. part of a nucleating agent composition [diacetal is 1,3:2,4-bis-O-(p-methylbenzylidene)-D-sorbitol (hereinafter abbreviated as "MD"); containing 1000 ppm of potassium p-methylbenzoate, 80 ppm of p-methylbenzaldehyde, and 0.2 wt. % of water], pellets and sheets were produced.

The degree of discoloration of the obtained pellets, the properties of the obtained sheets (haze, degree of discoloration and amount of generated aldehyde), diameter and proportion of the protofibrils, as well as the amount of the position isomers of diacetal in the above nucleating agent composition are shown in Table 1.

In Example 1 and other Examples and Comparative Examples and in Table 1, the alkali content, aldehyde content, water content, and the content of the position isomers of the diacetal are based on the nucleating agent composition.

The amount of generated aldehyde is based on the sheet.

The proportion of protofibrils in the recrystallized diacetal is the proportion (vol. %) of protofibrils based on all fibrils.

Example 2

Using 0.25 wt. part of a nucleating agent composition [diacetal is 1,3:2,4-bis-O-(3,4-dimethylbenzylidene)-D-sorbitol (hereinafter abbreviated as "DMD"); containing 800 ppm of potassium 3,4-dimethylbenzoate, 100 ppm of 3,4-dimethylbenzaldehyde, and 0.2 wt. % of water], pellets and sheets were produced.

The discoloration degree of the obtained pellets, and the properties of the sheets (haze, degree of discoloration and amount of generated aldehyde), diameter and proportion of the protofibrils, as well as the amount of the position isomers of the diacetal in the nucleating agent composition are shown in Table 1.

Example 3

Using 0.25 wt. part of a nucleating agent composition [diacetal is 1,3:2,4-bis-O-(2,4,5-trimethylbenzylidene)-D- sorbitol (hereinafter abbreviated as "TMD"); containing 200 ppm of potassium 3,4-dimethylbenzoate, 150 ppm of potassium hydroxide, 100 ppm of 2,4,5-trimethylbenzaldehyde, and 0.2 wt. % of water], pellets and sheets were produced.

The discoloration degree of the obtained pellets, and the properties of the sheets (haze, degree of discoloration and amount of generated aldehyde), diameter and proportion of the protofibrils, as well as the amount of the position isomers of the diacetal in the nucleating agent composition are shown in Table 1.

Example 4

Using 0.25 wt. part of a nucleating agent composition [diacetal is 1,3:2,4-bis-O-(4-ethylbenzylidene)-D-sorbitol (hereinafter abbreviated as "ED"); containing 50 ppm of potassium 4-ethylbenzoate, 50 ppm of potassium hydroxide, 100 ppm of 4-ethylbenzaldehyde, and 0.2 wt. % of water], pellets and sheets were produced.

The discoloration degree of the obtained pellets, and the properties of the sheets (haze, degree of discoloration and amount of generated aldehyde), diameter and proportion of the protofibrils, as well as the amount of the position isomers of the diacetal in the nucleating agent composition are shown in Table 1.

Example 5

Using 0.2 wt. part of a nucleating agent composition [diacetal is MD; containing 500 ppm of potassium hydroxide, 150 ppm of 4-methylbenzaldehyde, and 0.3 wt. % of water], pellets and sheets were produced.

The discoloration degree of the obtained pellets, and the properties of the sheets (haze, degree of discoloration and amount of generated aldehyde), diameter and proportion of the protofibrils, as well as the amount of the position isomers of the diacetal in the nucleating agent composition are shown in Table 1.

Example 6

Using 0.8 wt. part of a nucleating agent composition [diacetal is MD; containing 20 ppm of potassium hydroxide, 10 ppm of 4-methylbenzaldehyde, and 0.2 wt. % of water], pellets and sheets were produced.

The discoloration degree of the obtained pellets, and the properties of the sheets (haze, degree of discoloration and amount of generated aldehyde), diameter and proportion of the protofibrils, as well as the amount of the position isomers of the diacetal in the nucleating agent composition are shown in Table 1.

Example 7

Using 0.5 wt. part of a nucleating agent composition [diacetal is DMD; containing 40 ppm of sodium hydroxide, 100 ppm of 3,4-dimethylbenzaldehyde, and 0.1 wt. % of water], pellets and sheets were produced.

The discoloration degree of the obtained pellets, and the properties of the sheets (haze, degree of discoloration and amount of generated aldehyde), diameters and proportion of the protofibrils, as well as the amount of the position isomers of the diacetal in the nucleating agent composition are shown in Table 1.

Example 8

Using 0.5 wt. part of a nucleating agent composition [diacetal is TMD: containing 30 ppm of potassium trimethylbenzoate, 50 ppm of 2,4,5-trimethylbenzaldehyde, and 0.2 wt. % of water], pellets and sheets were produced.

The discoloration degree of the obtained pellets, and the properties of the sheets (haze, degree of discoloration and amount of generated aldehyde), diameter and proportion of the protofibrils, as well as the amount of the position isomers of the diacetal in the nucleating agent composition are shown in Table 1.

Example 9

Using 0.5 wt. part of a nucleating agent composition [diacetal is TMD; containing 40000 ppm of N,N-diethanolstearylamine, 50 ppm of 2,4,5-trimethylbenzaldehyde, and 0.2 wt. % of water], pellets and sheets were produced.

The discoloration degree of the obtained pellets, and the properties of the sheets (haze, degree of discoloration and amount of generated aldehyde), diameter and proportion of the protofibrils, as well as the amount of the position isomers of the diacetal in the nucleating agent composition are shown in Table 1.

Comparative Example 1

Pellets and sheets were produced without adding a nucleating agent composition.

The discoloration degree of the pellets and the properties of the sheets (haze, degree of discoloration, and the amount of generated aldehyde) are shown in Table 1.

Comparative Example 2

Using 5 wt. parts of a nucleating agent composition [diacetal is MD; containing 1 wt. % (10000 ppm) of potassium hydroxide, 180 ppm of 4-methylbenzaldehyde, and 0.3 wt. % of water], pellets and sheets were produced.

The discoloration degree of pellets and the properties of the sheets (haze, degree of discoloration and amount of generated aldehyde), diameter and proportion of the protofibrils, as well as the amount of the position isomers of the diacetal in the nucleating agent composition are shown in Table 1.

Comparative Example 3

Using 0.3 wt. part of a nucleating agent composition [diacetal is MD; containing 20 ppm of sodium carbonate, 300 ppm of 4-methylbenzaldehyde, and 0.3 wt. % of water], pellets and sheets were produced.

The discoloration degree of the obtained pellets and the properties of the sheets (haze, degree of discoloration and amount of generated aldehyde), diameter and proportion of the protofibrils, as well as the amount of the position isomers of the diacetal in the nucleating agent composition are shown in Table 1.

Comparative Example 4

Using 0.3 wt. part of a nucleating agent composition [diacetal is MD; containing 100 ppm of 4-methylbenzaldehyde and 0.2 wt. % of water; containing no alkaline compound], pellets and sheets were produced.

The discoloration degree of the obtained pellets and the properties of the sheets (haze, degree of discoloration and amount of generated aldehyde), diameter and proportion of the protofibrils, as well as the amount of the position isomers of diacetal in the nucleating agent composition are shown in Table 1.

Comparative Example 5

Using 0.3 wt. part of a nucleating agent composition [diacetal is DMD; containing 25 ppm of sodium carbonate, 100 ppm of 3,4-dimethylbenzaldehyde, and 2.5 wt. % of water], pellets and sheets were produced.

The discoloration degree of the obtained pellets and the properties of the sheets (haze, degree of discoloration and amount of generated aldehyde), diameter and proportion of the protofibrils, as well as the amount of the position isomers of the diacetal in the nucleating agent composition are shown in Table 1.

Comparative Example 6

Using 0.3 wt. part of a nucleating agent composition [diacetal is DMD; containing 5 ppm of sodium carbonate, 100 ppm of 3,4-dimethylbenzaldehyde, and 0.3 wt. % of water], pellets and sheets were produced.

The discoloration degree of the obtained pellets and the properties of the sheets (haze, degree of discoloration and amount of generated aldehyde), diameter and proportion of the protofibrils, as well as the amount of the position isomers of diacetal in the nucleating agent composition are shown in Table 1.

Comparative Example 7

Using 0.3 wt. part of a nucleating agent composition [diacetal is MD; containing 200 ppm of sodium carbonate, 10 ppm of p-methylbenzaldehyde, 0.1 wt. % of water, and 0.9 wt. % of diacetal isomers], pellets and sheets were produced.

The discoloration degree of the obtained pellets and the properties of the sheets (haze, degree of discoloration and amount of generated aldehyde), diameter and proportion of the protofibrils, as well as the amount of the position isomers of the diacetal in the nucleating agent composition are shown in Table 1.

Comparative Example 8

Using 0.3 wt. part of a nucleating agent composition [diacetal is DMD; containing 200 ppm of sodium carbonate, 15 ppm of 3,4-dimethylbenzaldehyde, 0.1 wt. % of water, and 1.2 wt. % of diacetal isomers], pellets and sheets were produced.

The discoloration degree of the obtained pellets and the properties of the sheets (haze, degree of discoloration and amount of generated aldehyde), diameter and proportion of the protofibrils, as well as the amount of the position isomers of the diacetal in the nucleating agent composition are shown in Table 1.

Comparative Example 9

Using 0.3 wt. part of a nucleating agent composition [diacetal is ED; containing 200 ppm of sodium carbonate, 10 ppm of p-ethylbenzaldehyde, 0.5 wt. % of water, and 0.9 wt. % of diacetal isomers], pellets and sheets were produced.

The discoloration degree of the obtained pellets and the properties of the sheets (haze, degree of discoloration and amount of generated aldehyde), diameter and proportion of the protofibrils, as well as the amount of the position isomers of the diacetal in the nucleating agent composition are shown in Table 1.

TABLE 1

| | | Trace components in the nucleating agent composition | | | | Properties of the sheet | | | | Protofibrils | |
|---|---|---|---|---|---|---|---|---|---|---|---|
| | Type of Nucleating agent/amount (phr) | Alkali amount (ppm) | Aldehyde amount (ppm) | Water content (wt. %) | Diacetal position isomers (wt. %) | Discoloration degree of pellets | Haze | Discoloration degree | Generated aldehyde amount (ppm) | Diameter (nm) | Proportion (%) |
| Ex. 1 | MD/0.25 | 1,000 | 80 | 0.2 | 0.2 | ○ | 9.8 | ○ | 1.0 | 10 | 80 |
| Ex. 2 | DMD/0.25 | 800 | 100 | 0.2 | 0.7 | ○ | 10.1 | ○ | 1.5 | 11 | 80 |
| Ex. 3 | TMD/0.25 | 350 | 100 | 0.2 | 0.2 | ○ | 12.0 | ○ | 1.0 | 10 | 80 |
| Ex. 4 | ED/0.25 | 100 | 100 | 0.2 | 0.1 | ○ | 14.2 | ○ | 1.0 | 11 | 85 |
| Ex. 5 | MD/0.2 | 500 | 150 | 0.3 | 0.1 | ○ | 10.1 | ○ | 1.0 | 10 | 80 |
| Ex. 6 | MD/0.8 | 20 | 10 | 0.2 | 0.1 | ○ | 10.1 | ○ | 1.0 | 10 | 75 |
| Ex. 7 | DMD/0.5 | 40 | 100 | 0.1 | 0.2 | ○ | 10.1 | ○ | 1.1 | 11 | 80 |
| Ex. 8 | TMD/0.5 | 30 | 50 | 0.2 | 0.1 | ○ | 12.0 | ○ | 1.0 | 10 | 80 |
| Ex. 9 | TMD/0.5 | 40,000 | 50 | 0.2 | 0.1 | ○ | 12.0 | ○ | 1.0 | 10 | 85 |
| Comp. Ex. 1 | Nucleating agent not added | — | — | — | — | ○ | 62.5 | ○ | 0 | — | — |
| Comp. Ex. 2 | MD/5 | 10,000 | 180 | 0.3 | 0.1 | x | Clouded | x | 2.5 | 60 | 5 |
| Comp. Ex. 3 | MD/0.3 | 20 | 300 | 0.3 | 0.9 | x | 9.5 | x | 3.0 | 16 | 80 |
| Comp. Ex. 4 | MD/0.3 | 0 | 100 | 0.2 | 0.1 | x | 12.5 | x | 4.8 | 12 | 80 |
| Comp. Ex. 5 | DMD/0.3 | 25 | 100 | 2.5 | 0.1 | x | 10.5 | x | 3.5 | 11 | 80 |
| Comp. Ex. 6 | DMD/0.3 | 5 | 100 | 0.3 | 0.1 | x | 10.3 | x | 4.0 | 11 | 80 |
| Comp. Ex. 7 | MD/0.3 | 200 | 10 | 0.1 | 0.9 | x | 9.7 | x | 3.1 | 11 | 80 |

TABLE 1-continued

| | Type of Nucleating agent/amount (phr) | Trace components in the nucleating agent composition | | | | Properties of the sheet | | | | Protofibrils | |
| --- | --- | --- | --- | --- | --- | --- | --- | --- | --- | --- | --- |
| | | Alkali amount (ppm) | Aldehyde amount (ppm) | Water content (wt. %) | Diacetal postion isomers (wt. %) | Discoloration degree of pellets | Haze | Discoloration degree | Generated aldehyde amount (ppm) | Diameter (nm) | Proportion (%) |
| Comp. Ex. 8 | DMD/0.3 | 200 | 15 | 0.1 | 1.2 | x | 11.0 | x | 3.8 | 11 | 80 |
| Comp. Ex. 9 | ED/0.3 | 200 | 10 | 0.5 | 0.9 | x | 12.5 | x | 4.0 | 12 | 80 |

Recrystallization of the diacetal under the conditions of the present invention significantly reduces the decomposition and disproportionation of the diacetal and discoloration of resins, so that the nucleating effects of the diacetal are produced to a maximum degree.

What is claimed is:

1. A method for recrystallizing a diacetal represented by the general formula (1)

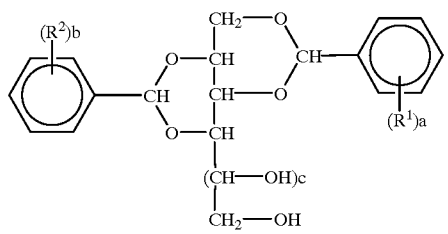

(1)

wherein $R^1$ and $R^2$ are the same or different and each represent a hydrogen atom, a $C_1$–$C_4$ alkyl group, a $C_1$–$C_4$ alkoxy group or a halogen atom; a and b each represent an integer of 1 to 5; c is 0 or 1; when a is 2, the two $R^1$ groups may optionally be taken together with the benzene ring to which they are attached to form a tetralin ring; and when b is 2, the two $R^2$ groups may optionally be taken together with the benzene ring to which they are attached to form a tetralin ring, in a polyolefin resin without giving a yellowish tint to the polyolefin resin, the method comprising:

(i) heating and melting a resin composition comprising (a) the polyolefin resin and (b) a nucleating agent composition containing at least one diacetal represented by the above formula (1) at a temperature not lower than the sol-gel transition temperature during the heating cycle of said resin composition, to give a molten resin composition in which said nucleating agent composition is uniformly dissolved in the molten polyolefin resin; and (ii) cooling the resulting molten resin composition; wherein (A) said nucleating agent composition contains 10 to 5000 ppm of at least one alkaline compound selected from the group consisting of alkali metal salts, alkali metal hydroxides, alkaline earth metal salts and alkaline earth metal hydroxides and/or 1000 to 80000 ppm of an organic amine;

(B) the total amount of
  (B-1) an aromatic aldehyde represented by the formula (2)

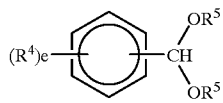

(2)

wherein $R^3$ represents a hydrogen atom, a $C_1$–$C_4$ alkyl group, a $C_1$–$C_4$ alkoxy group or a halogen atom; d is an integer of 1 to 5; when d is 2, the two $R^3$ groups may optionally be taken together with the benzene ring to which they are attached to form a tetralin ring, and (B-2) a dialkyl acetal represented by the formula (3)

$$(R^4)e-\bigcirc-CH\begin{matrix}OR^5\\OR^5\end{matrix}$$ (3)

wherein $R^4$ is a hydrogen atom, a $C_1$–$C_4$ alkyl group, a $C_1$–$C_4$ alkoxy group or a halogen atom; $R^5$ represents a $C_1$–$C_3$ alkyl group; e is an integer of 1 to 5; when e is 2, the two $R^4$ groups may optionally be taken together with the benzene ring to which they are attached to form a tetralin ring, in the nucleating agent composition is not higher than 400 ppm;

(C) water content of said nucleating agent composition is not higher than 1% by weight;

(D) said resin composition comprises said diacetal represented by the formula (1) at a concentration of 0.01 to 4 wt. % based on the total amount of said polyolefin resin and said diacetal; and (E) the proportion of one or more position isomers of the diacetal represented by the formula (1) in the nucleating agent composition is not higher than 0.7 wt. %.

2. The method according to claim 1, wherein the diacetal of the formula (1) is a compound represented by the formula (1) wherein $R^1$ and $R^2$ each represent a $C_1$–$C_4$ alkyl group or a halogen atom; a and b each are 1 or 2 or 3; and c is 1.

3. The method according to claim 1, wherein the diacetal represented by the formula (1) is at least one compound selected from the group consisting of:
1,3:2,4-bis-O-(benzylidene)-D-sorbitol,
1,3:2,4-bis-O-(p-methylbenzylidene)-D-sorbitol,
1,3:2,4-bis-O-(p-ethylbenzylidene)-D-sorbitol,
1,3:2,4-bis-O-(2,4-dimethylbenzylidene)-D-sorbitol,
1,3:2,4-bis-O-(3,4-dimethylbenzylidene)-D-sorbitol,
1,3:2,4-bis-O-(3,5-dimethylbenzylidene)-D-sorbitol,
1,3:2,4-bis-O-(2,4,5-trimethylbenzylidene)-D-sorbitol,
1,3:2,4-bis-O-(p-chlorobenzylidene)-D-sorbitol, 1,3:2,4-bis-O-(tetrahydronaphthylidene)-D-sorbitol,
1,3-O-benzylidene-2,4-O-(2,4-dimethylbenzylidene)-D-sorbitol,
1,3-O-(2,4-dimethylbenzylidene)-2,4-O-benzylidene-D-sorbitol,
1,3-O-benzylidene-2,4-O-(3,4-dimethylbenzylidene)-D-sorbitol, and
1,3-O-(3,4-dimethylbenzylidene)-2,4-O-benzylidene-D-sorbitol.

4. The method according to claim 1, wherein in the step of cooling said molten resin composition, said molten resin composition having a temperature not lower than its sol-gel transition temperature during the heating cycle is rapidly cooled to 10 to 80° C.

5. The method according to claim 1, wherein in the step of cooling said molten resin composition, said molten resin composition having a temperature not lower than its sol-gel transition temperature during the heating cycle is cooled by injection molding, press molding or extrusion molding in which the molten resin composition is rapidly cooled to 10 to 80° C.

6. The method according to claim 1, wherein the alkaline compound is at least one member selected from the group consisting of potassium hydroxide; sodium hydroxide; lithium hydroxide; sodium carbonate; potassium carbonate; sodium benzoate; potassium benzoate; sodium salt, potassium salt and lithium salt of benzoic acid having one or more alkyl groups, alkoxy groups or halogen atoms as the substituent(s); potassium salt, sodium salt and lithium salt of glutamic acid; and sodium salt and potassium salt of $C_1$–$C_{24}$ fatty acid and $C_2$–$C_{24}$ hydroxy-fatty acid.

7. The method according to claim 1, wherein the total amount of the aromatic aldehyde represented by the formula (2) and the dialkyl acetal represented by the formula (3) in the nucleating agent composition is not higher than 200 ppm.

8. A method for recrystallizing a diacetal represented by the formula (1)

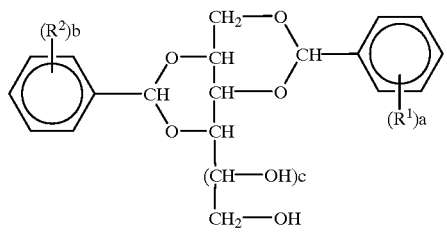

wherein $R^1$ and $R^2$ are the same or different and each represent a hydrogen atom, a $C_1$–$C_4$ alkyl group, a $C_1$–$C_4$ alkoxy group or a halogen atom; a and b each represent an integer of 1 to 5; c is 0 or 1; in a polyolefin resin, the method comprising:

(i) dissolving, in (a) a melt of the polyolefin resin, (b) a nucleating agent composition comprising at least one diacetal of the formula (1) to give a molten resin composition, and (ii) cooling the resulting molten resin composition,
wherein (A) said nucleating agent composition contains 10 to 5000 ppm of at least one alkaline compound selected from the group consisting of alkali metal salts, potassium hydroxide, sodium hydroxide and lithium hydroxide and/or 1000 to 80000 ppm of an organic amine;

(B) the total amount of
(B-1) an aromatic aldehyde represented by the formula (2)

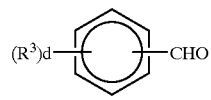

wherein $R^3$ represents a hydrogen atom, a $C_1$–$C_4$ alkyl group, a $C_1$–$C_4$ alkoxy group or a halogen atom; d is an integer of 1 to 5, and (B-2) a dialkyl acetal represented by the formula (3)

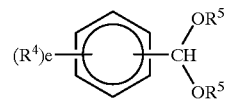

wherein $R^4$ is a hydrogen atom, a $C_1$–$C_4$ alkyl group, a $C_1$–$C_4$ alkoxy group or a halogen atom; $R^5$ represents a $C_1$–$C_3$ alkyl group; and e is an integer of 1 to 5 in the nucleating agent composition is not higher than 200 ppm;

(C) water content of said nucleating agent composition is not higher than 1 wt. %;

(D) the concentration of the diacetal represented by the formula (1) in the polyolefin resin is 0.01 to 4 wt.; and (E) the proportion of one or more position isomers of the diacetal represented by the formula (1) in the nucleating agent composition is not higher than 0.7 wt. %.

9. The method according to claim 8, wherein the diacetal represented by the formula (1) is at least one compound selected from the group consisting of:
1,3:2,4-bis-O-(benzylidene)-D-sorbitol,
1,3:2,4-bis-O-(p-methylbenzylidene)-D-sorbitol,
1,3:2,4-bis-O-(p-ethylbenzylidene)-D-sorbitol,
1,3:2,4-bis-O-(2,4-dimethylbenzylidene)-D-sorbitol,
1,3:2,4-bis-O-(3,4-dimethylbenzylidene)-D-sorbitol,
1,3:2,4-bis-O-(2,4,5-trimethylbenzylidene)-D-sorbitol, and
1,3:2,4-bis-O-(p-chlorobenzylidene)-D-sorbitol.

10. The method according to claim 8, wherein the molten resin composition is adjusted to a temperature of not lower than its sol-gel transition temperature during the heating cycle, and then the molten resin composition is cooled by injection molding, press molding or extrusion molding in which the molten resin composition is rapidly cooled to 20 to 80° C.

11. Diacetal crystals present in a polyolefin resin molded article in the form of fibrils, wherein protofibrils 9 to 20 nm in diameter are present in an amount of 50 vol. % or more based on all fibrils, the diacetal being represented by the formula (1)

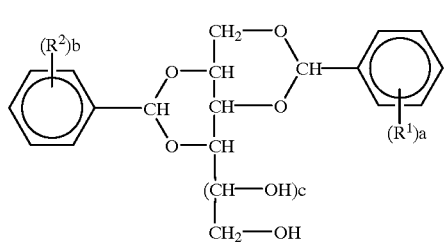

(1)

wherein $R^1$ and $R^2$ are the same or different and each represent a hydrogen atom, a $C_1$–$C_4$ alkyl group, a $C_1$–$C_4$ alkoxy group or a halogen atom; a and b each represent an integer of 1 to 5, preferably 1 to 3; c is 0 or 1;

when a is 2, the two $R^1$ groups may optionally be taken together with the benzene ring to which they are attached to form a tetralin ring; and when b is 2, the two $R^2$ groups may optionally be taken together with the benzene ring to which they are attached to form a tetralin ring.

12. A molded article comprising (a) a polyolefin resin, and (b) (b-1) diacetal crystals present in the polyolefin resin in the form of fibrils composed of protofibrils 9 to 20 nm in diameter, or (b-2) diacetal crystals present in the polyolefin resin in the form of fibrils composed of mixed crystals comprising protofibrils 9–20 nm in diameter and bundled crystals, the bundled crystals consisting of protofibrils 9–20 nm in diameter assembled in the form of bundles, the diacetal being represented by the formula (1)

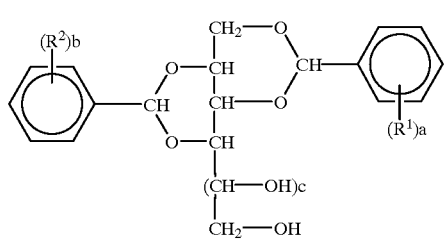

(1)

wherein $R^1$ and $R^2$ are the same or different and each represent a hydrogen atom, a $C_1$–$C_4$ alkyl group, a $C_1$–$C_4$ alkoxy group or a halogen atom; a and b each represent an integer of 1 to 5, preferably 1 to 3; c is 0 or 1;

when a is 2, the two $R^1$ groups may optionally be taken together with the benzene ring to which they are attached to form a tetralin ring; and when b is 2, the two $R^2$ groups may optionally be taken together with the benzene ring to which they are attached to form a tetralin ring.

13. A process for producing polyolefin resin pellets substantially free from a yellowish tint, the pellets containing a diacetal recrystallized in the polyolefin resin and represented by the formula (1)

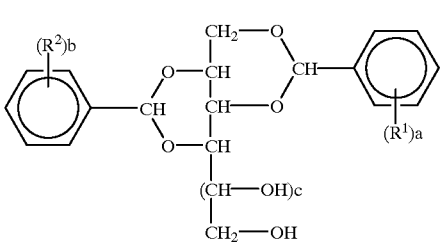

(1)

wherein $R^1$ and $R^2$ are the same or different and each represent a hydrogen atom, a $C_1$–$C_4$ alkyl group, a $C_1$–$C_4$ alkoxy group or a halogen atom; a and b each represent an integer of 1 to 5; c is 0 or 1;

when a is 2, the two $R^1$ groups may optionally be taken together with the benzene ring to which they are attached to form a tetralin ring; and when b is 2, the two $R^2$ groups may optionally be taken together with the benzene ring to which they are attached to form a tetralin ring, the method comprising:

(i) heating and melting a resin composition comprising (a) a polyolefin resin and (b) a nucleating agent composition comprising at least one of the diacetal represented by the formula (1) at a temperature not lower than a sol-gel transition temperature during the heating cycle of the resin composition to give a molten resin composition in which the nucleating agent composition is uniformly dissolved in the molten polyolefin resin;

(ii) extruding the obtained molten resin composition and cooling the extrudate; and (iii) cutting the thus-obtained strand of the polyolefin resin containing the recrystallized diacetal, wherein (A) the nucleating agent composition contains 10 to 5000 ppm of at least one alkaline compound selected from the group consisting of alkali metal salts, alkali metal hydroxides, alkaline earth metal salts and alkaline earth metal hydroxides and/or 1000 to 80000 ppm of an organic amine;

(B) the total amount of (B-1) an aromatic aldehyde represented by the formula (2)

(2)

wherein $R^3$ represents a hydrogen atom, a $C_1$–$C_4$ alkyl group, a $C_1$–$C_4$ alkoxy group or a halogen atom; d is an integer of 1 to 5; when d is 2, the two $R^3$ groups may optionally be taken together with the benzene ring to which they are attached to form a tetralin ring, and (B-2) a dialkyl acetal represented by the formula (3)

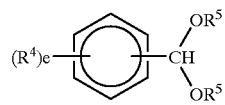

(3)

wherein $R^4$ represents a hydrogen atom, a $C_1$–$C_4$ alkyl group, a $C_1$–$C_4$ alkoxy group or a halogen atom; $R^5$ represents a $C_1$–$C_3$ alkyl group; e is an integer of 1 to 5; when e is 2, the two $R^4$ groups may optionally be taken together with the benzene ring to which they are attached to form a tetralin ring, in the nucleating agent composition is not higher than 400 ppm, (C) water content of said nucleating agent composition is not higher than 1 wt. %;

(D) the resin composition contains 0.01 to 4 wt. % of the diacetal represented by the formula (1), relative to the total amount of the polyolefin resin and the diacetal; and (E) the proportion of one or more position isomers of the diacetal represented by the formula (1) in the nucleating agent composition is not higher than 0.7 wt. %.

14. Polyolefin resin pellets substantially free from a yellowish tint, the pellets being obtainable by the process as defined in claim 13.

15. A process for producing a polyolefin resin molded article substantially free from a yellowish tint, the molded article comprising (a) the polyolefin resin, and (b) (b-1) diacetal crystals present in the polyolefin resin in the form of fibrils composed of protofibrils 9 to 20 nm in diameter, or (b-2) diacetal crystals present in the polyolefin resin in the form of fibrils composed of mixed crystals comprising protofibrils 9 to 20 nm in diameter and bundled crystals, the bundled crystals comprising said protofibrils assembled in the form of bundles, the method comprising the steps of:

(i) heating the polyolefin resin pellets as defined in claim 14 at a temperature not lower than the sol-gel transition temperature during the heating cycle thereof to give a melt in the form of a sol; and (ii) carrying out injection-, press- or extrusion-molding in which said melt is rapidly cooled to a temperature of 10 to 80° C., the diacetal being represented by the formula (1)

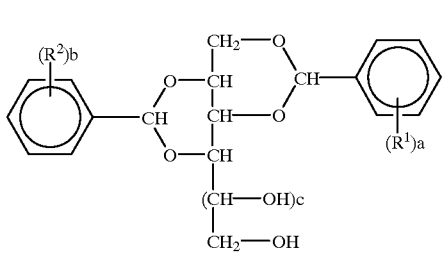

(1)

wherein $R^1$ and $R^2$ are the same or different and each represent a hydrogen atom, a $C_1$–$C_4$ alkyl group, a $C_1$–$C_4$ alkoxy group or a halogen atom; a and b each represent an integer of 1 to 5; c is 0 or 1;

when a is 2, the two $R^1$ groups may optionally be taken together with the benzene ring to which they are attached to form a tetralin ring; and when b is 2, the two $R^2$ groups may optionally be taken together with the benzene ring to which they are attached to form a tetralin ring.

16. A molded article obtainable by the process as defined in claim 15.

* * * * *